United States Patent [19]

Bankston

[11] Patent Number: 4,551,677
[45] Date of Patent: Nov. 5, 1985

[54] APPARATUS AND METHOD FOR INSPECTING A BEARING BALL

[75] Inventor: Benjamin F. Bankston, Huntsville, Ala.

[73] Assignee: The United States of America as represented by the Administrator of the National Aeronautics and Space Administration, Washington, D.C.

[21] Appl. No.: 473,827

[22] Filed: Mar. 9, 1983

[51] Int. Cl.⁴ .................. G01N 27/90; G01B 7/28
[52] U.S. Cl. .................... 324/226; 324/238; 324/240; 324/262; 73/37.5
[58] Field of Search .............. 324/207, 208, 209, 226, 324/228–231, 233–243, 262; 73/37.5, 37.6

[56] References Cited

U.S. PATENT DOCUMENTS

| | | | |
|---|---|---|---|
| 2,408,672 | 10/1946 | Mennesson | 73/37.5 UX |
| 3,244,972 | 4/1966 | Fisher | 324/226 |
| 3,358,225 | 12/1967 | Peugeot | 324/234 X |
| 3,361,961 | 1/1968 | Zoellick | 324/234 X |
| 3,732,726 | 5/1973 | Ferber | 324/226 X |
| 3,872,378 | 3/1975 | Shiraiwa et al. | 324/226 |
| 4,155,455 | 5/1979 | Spierer et al. | 324/232 X |
| 4,430,614 | 2/1984 | Gereg | 324/262 X |

FOREIGN PATENT DOCUMENTS

| | | | |
|---|---|---|---|
| 2004628 | 8/1971 | Fed. Rep. of Germany | 73/37.5 |
| 2103637 | 8/1972 | Fed. Rep. of Germany | |
| 1381392 | 1/1975 | United Kingdom | |
| 645071 | 1/1979 | U.S.S.R. | 324/239 |
| 693291 | 10/1979 | U.S.S.R. | 324/240 |

*Primary Examiner*—Gerard R. Strecker
*Assistant Examiner*—Warren S. Edmonds
*Attorney, Agent, or Firm*—Joseph H. Beumer; John R. Manning; Leon D. Wofford, Jr.

[57] ABSTRACT

A method and apparatus for inspecting the surface of a bearing ball is disclosed which includes a base (A) having a high friction non-abrasive base scanning surface (12). A holding device (B) includes a cone-shaped cup recess (14) in which a ball element (18) is received. Air is introduced through a passage (26) to relieve friction between the wall (16) of the recess and the ball element and facilitate rolling of the ball over the high friction base surface. The holding device is moved over the base scanning surface in a predetermined pattern (50) such that the entire surface of the ball element is inspected by an eddy current probe (C) which detects any surface defects.

15 Claims, 3 Drawing Figures

APPARATUS AND METHOD FOR INSPECTING A BEARING BALL

ORIGIN OF THE INVENTION

The invention described herein was made by an employee of the U.S. Government and may be manufactured and used by or for the Government for governmental purposes without the payment of any royalties thereon or therefor.

BACKGROUND OF THE INVENTION

The invention relates to the inspection of bearing balls. In the manufacture of bearing balls such as in the aerospace and aircraft industry, an assessment of the condition and appearance of the ball is required for reliable operation. In many applications of the bearing balls, such as in the main shaft of an aeroengine, defects and faults in the bearing ball may lead to premature failure of the bearing and subsequent damage or destruction.

The accurate inspection of the entire bearing surface of the ball is a problem which has given the manufacturer considerable trouble. Due to the minute nature of the possible defects including overheating cracks, unequal distribution of carbon, marks from oxidation, corrosion pitting and hard impact marks, and indentations the problem is compounded. The small size of the bearing ball necessitates accurate control of the inspection process in order to insure that the entire surface of the bearing ball is inspected.

In one prior method, an automatic feed mechanism passes balls through a cleaning tank into an oil immersion tank where they are picked up by an electric drive mechanism. While being continuously rotated, the balls are subjected to ultra sound which both refracts at the surface of the ball and propagates into the ball. If the wave meets a flaw, it is reflected back along its path, detected, displayed on a cathode ray tube and recorded on an ultraviolet chart. However, this technique requires immersion of the ball, probe, and an elaborate ball positioning mechanism in a fluid tank and is limited to larger ball diameters. Because of the requirement of a fluid couplant, periodic attendant cleaning of the equipment is required. Very sophisticated, and costly equipment is thus required. The complexity of the equipment subjects the inspection process to unreliability.

In another prior technique, three independently driven rollers were utilized to roll the bearing ball while in the proximity of a probe. A separate motor drive was required for each of the rollers which are then driven in a manner which would most likely assure inspection coverage of the ball. However, in order to control the ball movement elaborate control of the roller motors was required.

SUMMARY OF THE INVENTION

Accordingly, an important object of the present invention is to provide an effective method and apparatus for inspecting bearing balls for surface and near surface cracks, voids, and material anomalies with a minimum of tooling and a high reliability of detection.

The above object is accomplished according to the present invention by utilizing an eddy current inspection concept.

The apparatus includes a non-abrasive, high friction base scanning surface and a holding device which employs an inverted cone-shaped cup. Friction between the surface of the cone-shaped cup and the bearing ball is reduced by creating a surface layer of pressurized air adjacent the surface of the cone-shaped cup. Regulated air is delivered through a passage in the holding device that communicates with the recess of the cone-shaped cup. The eddy current probe is positioned centrally along an axis of the cone extending inwardly thereto. The holding device and bearing ball are moved over the base scanning surface in a predetermined pattern so that the entire surface area of the bearing ball is inspected by the probe. Due to the relative differences between the low friction air surface within the cone-shaped cup and the high friction of the base surface, the bearing ball rolls reliably and centrally within the recess of the cone-shaped cup for inspection.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
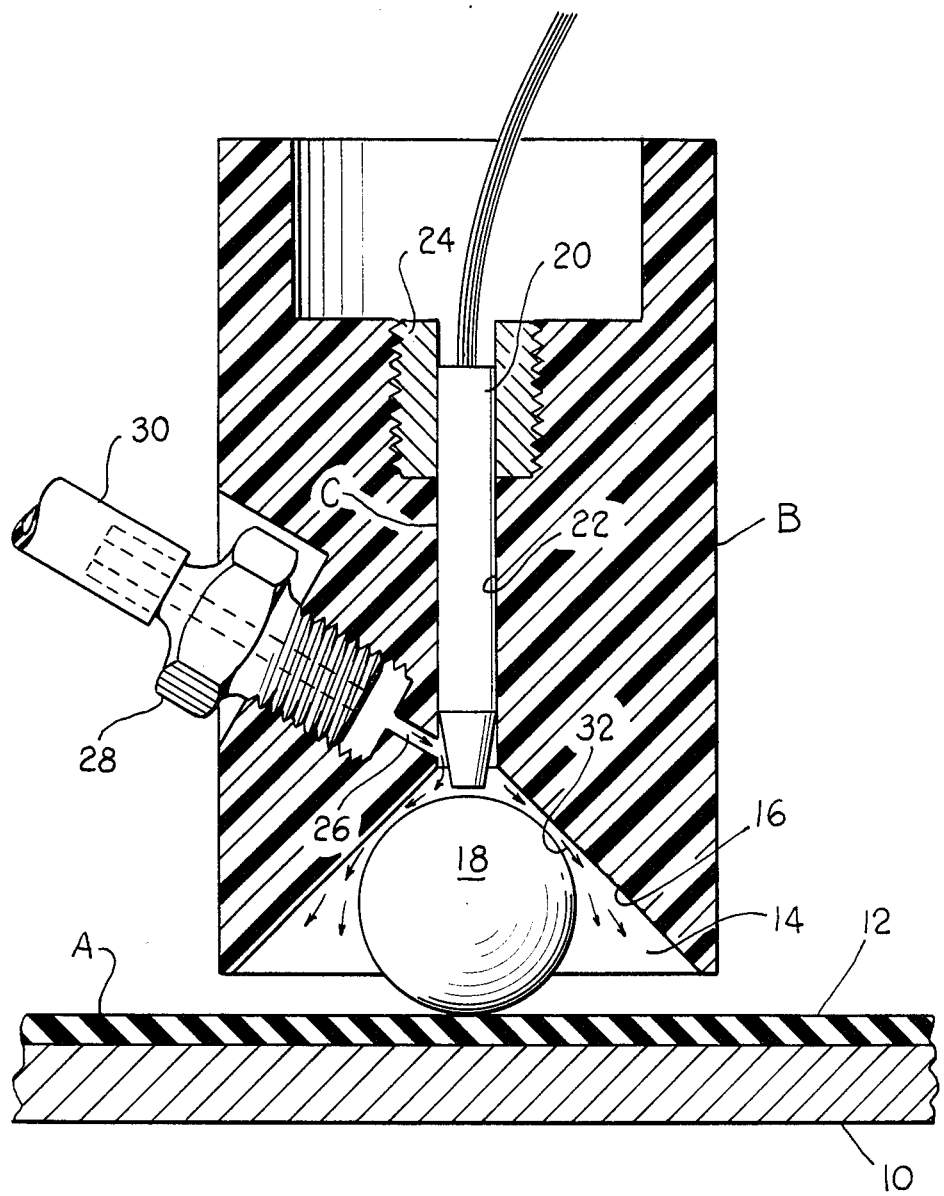
FIG. 1 is an enlarged elevational view showing the apparatus and method of the present invention in section.

Apparatus for inspecting a spherical element such as a bearing ball and the like for surface defects is illustrated as including a base means A having a high friction, non-abrasive scanning surface. A holding device B for retaining the spherical element in a low friction environment for movement over the high friction scanning surface is provided which includes an element retaining recess. The element retaining recess is defined by a tapered recess wall which tapers upwardly and inwardly to provide a progressively reducing cross-section for accommodating different size spherical elements. The recess is open at one end for receiving the element and a probe means C is carried centrally along an axis of the recess for detecting surface defects in the spherical element. Means is provided for creating a low pressure air layer adjacent the wall of the recess to relieve the friction against the spherical element during scanning operations. The relative differences between the high friction base surface and the low friction air surface facilitates rolling of the ball for reliable inspection of its entire surface.

Any suitable mechanical X-Y scanning device may be utilized as a means for moving the holding device and establishing a predetermined pattern over which the bearing ball is moved on the base surface during the scanning operation. Alternately, means for moving the holding device over a predetermined pattern may be provided by manually holding the holding device and moving the holding device over a pattern imprinted onto the base surface. The relative frictional forces produced on the spherical element between the low pressure air surface layer and the high friction base surface imparts a rolling movement to the spherical element. By moving the spherical element over a predetermined pattern, inspection of the entire surface of the spherical element by the probe means is assured. By making the width of the scan increments in both the X and Y directions greater than the diameter of the bearing ball inspection of the entire surface of the bearing ball may be achieved.

Referring now in more detail to the drawings, base means A is illustrated as including a base plate 10 and a non-abrasive high friction surface 12 which may be any suitable rubber material. The rubber will not let the bearing ball slip. The friction of the rubber is high and the friction in the holding device recess is low so that the movement of the holding device will govern the area of the ball that is inspected at any time. The high friction on the rubber base plate and low friction on the bearing ball as supported by the air in the holding device recess make positioning of the ball in relation to the probe accurately controlled by movement over the base plate.

The holding device B includes a contoured recess space in the form of a cone-shaped cup recess 14. The recess 14 is in the shape of an inverted cone and is defined by an upwardly and inwardly tapered wall 16 formed in a housing of the holding device which provides a progressively reducing cross-section for accommodating different size bearing balls 18. Probe means C includes an eddy current detecting probe 20 for inspecting the surface of the bearing ball 18. The eddy current probe 20 is carried along an axis of the inverted cone-shaped cup recess 14. The eddy current is carried in a central bore 22 formed in the housing of the holding device by means of a threaded plug 24. The probe is fixed to the plug and the plug may be adjusted in the holding device B such that the spacing between the end of the probe and the bearing ball may be adjusted. In practice, the eddy current probe is spaced approximately three mils from the surface of the bearing ball.

An air passage 26 is formed in the holding device B having a port opening communicating with recess 14 for delivering a flow of pressurized air into the recess. An air entrance nozzle 28 is threadably secured in the holding device B and includes a section of tubing 30 which may be connected to a source of pressurized air. A regulated air supply delivers air through the passage 26 into the recess at a sufficient pressure so that there is generally no friction on the ball surface on the one side thereof and high friction on the rubber contacting side of the ball whereby the ball rolls. Air introduced at approximately 1 psi provides a surface layer of air 32 around the wall 16 which keeps the ball from dragging on the surface of the recess wall.

Figure 3:
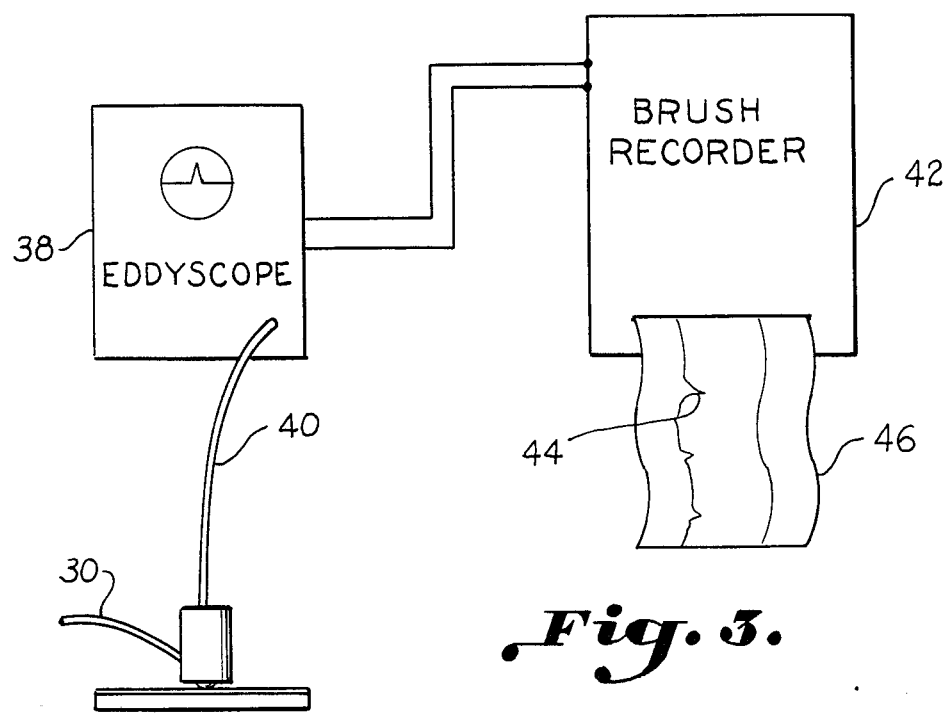
FIG. 3 is a schematic view illustrating operation of the method and apparatus according to the present invention.
Figure 2:
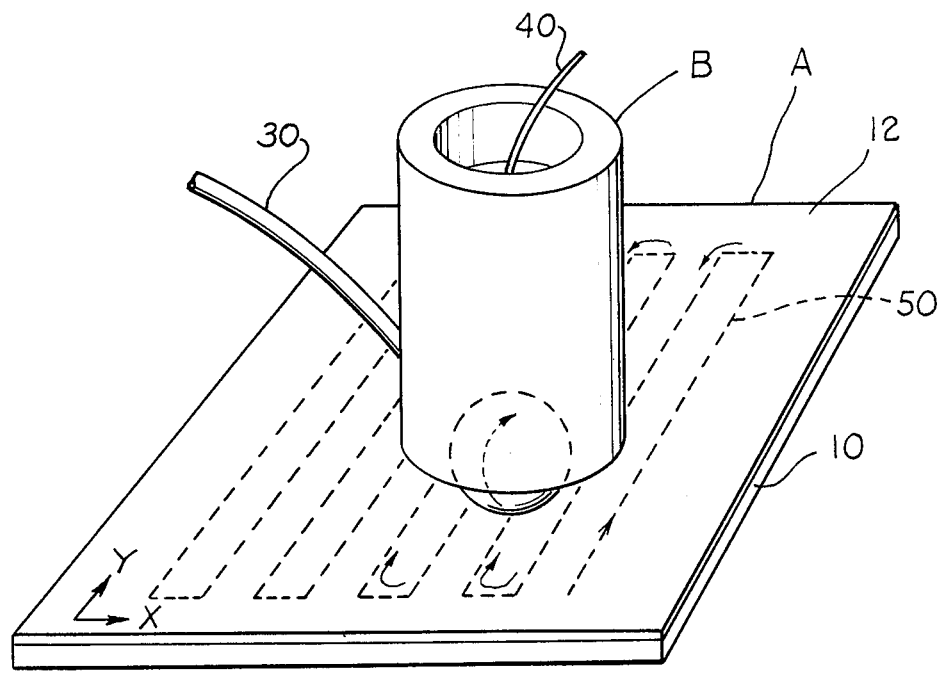
FIG. 2 is a perspective view illustrating a holding device and base scanning surface constructed according to the present invention.

A suitable detection and recording system may be provided for detecting the defects in the bearing ball surface and recording the defects as can best be seen in FIG. 3. For example, a conventional eddyscope 38 may be connected to the probe via leads 40 which includes a balance bridge circuit which varies depending upon the current around the surface of the ball as detected by probe 20. The current changes in response to surface variations and defects. Any suitable eddyscope may be utilized such as that manufactured by The Nortech Instrument Co., of Kennewick, Wash. as Model NDT15.

The eddyscope is connected to a recording device such as a Mark 280 strip chart recorder manufactured by The Clevite Corp. of Cleveland, Ohio. The bridge imbalance in the eddyscope caused by defects in the bearing ball surface results in a spike being recorded on the recorder 42 which may be displayed on a suitable strip chart recording medium 46.

As described above, the holding device B may be suitably attached to an arm of any suitable conventional X-Y mechanical scanning device (not shown) or may be moved manually by hand. The holding device is moved according to the predetermined pattern 50 established by the X-Y scanning device which can be set to move the holding device in any size increments of movement. If the holding device is moved by a mechanical scanning device, a spring loaded mount between the arm of the scanning device and the holding device is preferred for protection. The air pressure will adjust itself should the scanning base surface not be perfectly level and the holding device will float. If moved manually by hand, a predetermined pattern 50 may be imprinted on the base surface 12.

The predetermined pattern includes scan increments in the X-direction of eighty percent of the effective width of the probe. Thus, some overlap is permitted such that inspection of the entire surface of the ball bearing is achieved given a sufficient number of such increments. The holding device is moved in the Y direction in increments generally equal to the circumference of the bearing ball plus ten percent. This assures a small degree of overlap in the circumferential dimension upon each incremental movement in the X-direction facilitating scanning of the entire surface of the bearing ball. Thus, accurate control of the inspection technique and inspection of one-hundred percent of the bearing ball surface is achieved.

While a preferred embodiment of the invention has been described using specific terms, such description is for illustrative purposes only, and it is to be understood that changes and variations may be made without departing from the spirit or scope of the following claims.

I claim:

1. Apparatus for inspecting a spherical element such as a bearing ball and the like for surface defects comprising:
   base means having a high-friction, non-abrasive base scanning surface;
   a holding device having a housing for retaining said spherical element in a low-friction environment which includes a low pressure air layer which retains said spherical element for movement over said scanning surface;
   an element retaining recess included in said holding device defined by a tapered recess wall tapering upwardly and inwardly to provide a progressively reducing cross-section which receives and accommodates a spherical element of different sizes for retention and movement with said holding device;
   said recess including an enlarged open end for receiving said spherical element;
   a defect-detecting probe means carried by said holding device extending into said recess in proximity to said spherical element for detecting surface defects in said spherical element;
   means for delivering a flow of low pressure air into said recess and creating said low pressure air surface layer adjacent said wall of said recess to relieve the friction between said spherical element and said recess wall while effectively retaining said spherical element during scanning movement over said high-friction base scanning surface;

means establishing a predetermined pattern over which said holding device moves and said spherical element rolls over said base scanning surface during said scanning operation;

means for moving said holding device over said predetermined pattern;

relative frictional forces produced on said spherical element between said low-friction air surface layer and said high-friction scanning base surface imparting a rolling movement to said spherical element; and said spherical element being rolled and moved by said holding device over said base scanning surface according to said predetermined pattern whereby the entire surface of said spherical element is inspected by said defect-detecting probe means for surface defects.

2. The apparatus of claim 1 wherein said means for creating a low-friction air layer comprises:

an air passage formed in said housing of said holding device;

one end of said air passage adapted for connection to a source of low pressure air; and an opposite end of said air passage including a port opening into said recess opening in fluid communication with said recess.

3. The apparatus of claim 1 wherein said means for establishing said predetermined pattern includes a pattern established on said base scanning surface.

4. The apparatus of claim 1 wherein said high-friction, non-abrasive base surface includes a layer of rubber material carried on said base means.

5. The apparatus of claim 1 wherein said recess is shaped as an inverted cone-shaped cup element having its vertex pointed upwards, said probe means being axially aligned along an axis of the cone of said cone-shaped element.

6. The apparatus of claim 1 wherein said predetermined pattern includes scanning increments in an X-direction slightly less than the effective detection width of said probe means and scanning increments in a Y-direction greater than the circumference of the spherical element, and a sufficient number of said scanning increments in said X and Y directions so that a sufficient overlap of inspection coverage is permitted to insure inspection of 100% of the spherical element.

7. The apparatus of claim 6 wherein said scanning increment in the X-direction are approximately 80% of the effective width of said probe means and said scanning increments in said Y-direction amount to the circumference of the spherical element plus 10% of said circumference.

8. The apparatus of claim 1 wherein said probe means is an eddy current device.

9. A method for inspecting a bearing ball and the like spherical element for surface defects comprising:

providing a high-friction, non-abrasive base scanning surface;

providing a holding device having a retaining recess in which said bearing ball is retained;

providing a low-friction surface against a wall of said recess which is contacted by said spherical element for retention in said recess, said low-friction surface having a lower coefficient of friction than said base scanning surface;

providing a probe defect detecting means in said holding device adjacent said bearing ball for detecting surface defects in said bearing ball surface; and moving said holding device and bearing ball over said high-friction scanning surface in a predetermined pattern which presents the entire surface of said bearing ball to said defect detecting probe means.

10. The method of claim 9 including delivering a low pressure fluid into said retaining recess to relieve the friction in said retaining recess on said bearing ball and creates a low-friction fluid layer which provides said low-friction surface.

11. The method of claim 9 including providing said recess space in the form of a generally cone-shaped recess having a progressively reducing cross-section tapering away from said base scanning surface for accommodating different size bearing balls.

12. Apparatus for inspecting a bearing ball and the like for surface defects comprising:

a base;

a high-friction, non-abrasive base surface carried on said base;

a holding device for retaining said bearing ball and moving said ball over said base surface;

an element retaining recess formed in a housing of said holding device defined by a contoured recess space formed in said holding device having an open end for receiving said bearing ball;

probe means carried by said holding device communicating with said recess space for detecting surface defects in said bearing ball;

means for delivering a low pressure fluid into said recess space and creating a low pressure fluid cushion layer inside said recess space against which said bearing ball is held and retained, said fluid cushion effectively relieving friction on said bearing ball to provide a low friction on the retained side of said ball while a contact side of said bearing ball encounters high friction against said base surface;

said low friction on said retained side of said bearing ball and said high friction on said contact side of said ball facilitating rolling of said ball upon movement of said holding device;

means for moving said bearing in a predetermined pattern over said base surface during said inspection operation; and said bearing ball being rolled and moved by said holding device over said base surface according to said predetermined pattern whereby the entire surface of said spherical element is inspected by said probe means for surface defects.

13. The apparatus of claim 12 wherein said means for creating a low-friction cushion layer comprises:

an air passage formed in said housing of said holding device;

one end of said air passage adapted for connection to a source of low pressure air; and an opposite end of said air passage including a port opening into said recess space in fluid communication with said recess space.

14. The apparatus of claim 12 wherein said recess is shaped as an inverted cone-shaped cup element tapering inwardly from said open end, said probe means being carried along an axis of the cone of said cone-shaped element.

15. The apparatus of claim 12 wherein said probe means is an eddy current device.

* * * * *